(12) United States Patent
Patterson et al.

(10) Patent No.: US 11,282,592 B2
(45) Date of Patent: Mar. 22, 2022

(54) HEALTHCARE INFORMATION SYSTEM AND METHOD FOR CONTROLLING ACCESS TO A DATA PROJECTION

(71) Applicant: Change Healthcare Holdings, LLC, Nashville, TN (US)

(72) Inventors: Chris Patterson, Oakland, CA (US); Arien Malec, Oakland, CA (US)

(73) Assignee: CHANGE HEALTHCARE HOLDINGS, LLC, Nashville, TN (US)

(*) Notice: Subject to any disclaimer, the term of this patent is extended or adjusted under 35 U.S.C. 154(b) by 939 days.

(21) Appl. No.: 14/673,971

(22) Filed: Mar. 31, 2015

(65) Prior Publication Data
US 2016/0292357 A1 Oct. 6, 2016

(51) Int. Cl.
*G16H 10/60* (2018.01)
(52) U.S. Cl.
CPC .................. *G16H 10/60* (2018.01)
(58) Field of Classification Search
CPC ......... G06Q 50/22; G06Q 50/24; G16H 10/60
See application file for complete search history.

(56) References Cited

U.S. PATENT DOCUMENTS

| | | |
|---|---|---|
| 7,653,634 B2 | 1/2010 | Mathur |
| 8,583,686 B2 | 11/2013 | McGregor |
| 2003/0110212 A1* | 6/2003 | Lewis ............... H04L 45/04 709/203 |
| 2003/0188021 A1* | 10/2003 | Challenger ....... G06F 17/30896 709/246 |
| 2005/0137986 A1* | 6/2005 | Kean .................. G07F 7/1016 705/65 |

(Continued)

FOREIGN PATENT DOCUMENTS

EP   1193588 A2 * 4/2002 ......... G06F 12/1408

OTHER PUBLICATIONS

Bonatti, P., "An algebra for composing access control policies," ACM Transactions on Information and System Security, vol. 5, Issue 1, Feb. 2002, pp. 1-35, https://doi.org/10.1145/504909.504910 (Year: 2002).*

(Continued)

*Primary Examiner* — Lena Najarian
(74) *Attorney, Agent, or Firm* — 50-0220

(57) ABSTRACT

A healthcare information system, method and computer program product are provided to receive, process and output healthcare data in compliance with data use restrictions associated with the healthcare data, even in instances in which data projections are assembled from the data elements. In regards to a healthcare information system, processing circuitry is configured to assemble the data projection from a plurality of data elements. At least some data elements have different data use restrictions associated therewith. The processing circuitry is also configured to determine a combined data use restriction for the data projection based upon the data use restrictions of the data elements from which the data projection is assembled. The processing circuitry is further configured to associate metadata with the data projection including the combined data use restriction. Further, the processing circuitry is configured to control access to the data projection in accordance with the combined data use restriction.

23 Claims, 4 Drawing Sheets

(56) References Cited

U.S. PATENT DOCUMENTS

2006/0004745 A1* 1/2006 Kuhn ..................... G16H 15/00
2006/0080316 A1* 4/2006 Gilmore ............ G06F 17/30864
2007/0061393 A1   3/2007 Moore
2009/0187585 A1* 7/2009 Mathur ............... G06F 17/2211
2013/0297224 A1* 11/2013 Staib ..................... G09B 23/28
                                                          702/21

OTHER PUBLICATIONS

Wang, F et al., *A Framework for Mining Signatures from Event Sequences and Its Applications in Healthcare Data*, IEEE Transactions on Pattern Analysis and Machine Intelligence, vol. 35, No. 2 (Feb. 2013) 272-285.

\* cited by examiner

HEALTHCARE INFORMATION SYSTEM AND METHOD FOR CONTROLLING ACCESS TO A DATA PROJECTION

TECHNOLOGICAL FIELD

An example embodiment of the present invention relates generally to a healthcare information system and method and, more particularly, to a healthcare information system, method and computer program product for controlling access to a data projection.

BACKGROUND

Healthcare information systems receive, process and output a wide variety of healthcare data. For example, healthcare information systems may work with different types of healthcare data including data relating to the medical history of a patient, clinical data, patient data defining the birth date, address and other personal information, data relating to the result of various tests or procedures or the like. The healthcare data may be received by healthcare information systems from a wide variety of sources and the healthcare information systems may, in turn, provide output to a wide variety of recipients. For example, healthcare information systems may receive and/or provide data to various healthcare providers, patients, laboratories, pharmaceutical companies or the like.

Healthcare data is frequently associated with time. Consequently, the healthcare data that is operative may change from time to time, such as an instance in which the condition of a patient changes, assertions of facts are received that are in contradiction to previously received data, the privacy status of a patient's healthcare data changes or the like. A healthcare information system must therefore be able to determine the effective healthcare data at any point in time. In some instances, data may be received by a healthcare information system with each data element associated with a sequential moment in time. However, such sequentially captured data may sometimes be received by the healthcare information system out of order such that the sequence in which the data elements is received does not correspond to the actual sequence of the data elements. Some healthcare information systems therefore include relatively complex logic that endeavors to reconstruct the proper sequence of data elements in an instance in which the data elements are received in a different order. Such complex logic may adversely impact the efficiency with which the healthcare information system performs and the reliability of the information provided by the healthcare information system.

A healthcare information system may utilize the data for various purposes which may vary dramatically depending upon the recipient of the information from the healthcare information system. In this regard, patients within a distributed healthcare environment may experience healthcare events repeatedly. These events may include new healthcare encounters, pharmacy dispensing events, changes in healthcare status, and new data from a personal medical device or other wearable monitoring device. Data associated with each of these healthcare events may be received by a healthcare information system. The healthcare information system may then coordinate the provision of the data to one or more recipients, perform or update analytics based upon the additional data or otherwise generate composite data based upon the data that has been received. As a result of the wide variety of data and the repeated receipt of new data from various sources in a distributed healthcare environment, a healthcare information system may be burdened in order to receive, analyze and provide information relating to the data in a timely manner.

The use and provision of healthcare data by a healthcare information system are also complicated by the varying degrees of privacy associated with healthcare data. For example, a significant portion of healthcare data has a privacy level that is governed by the Health Insurance Portability and Accountability Act (HIPAA). However, some healthcare data is subject to greater levels of privacy based upon, for example, the data type, the data source or the recipient. For example, healthcare data related to mental health and/or substance abuse may be subject to heightened levels of privacy. Further, healthcare data provided by organizations, such as military organizations, that have more restrictive confidentiality requirements may also be subject to heightened levels of privacy. While processing and distributing the healthcare data in a manner compliant with the privacy level of the respective data elements is a significant undertaking, healthcare information systems frequently perform analytics or otherwise process the healthcare data in a manner that combines multiple data elements, each of which may have a respective privacy level associated therewith. In these instances, a healthcare information system may face even greater challenges in utilizing and providing such compilations of healthcare data in a manner that respects the respective privacy levels associated with each data element within the compilation. In this regard, healthcare information systems must generally balance a desire brought about by compliance with data privacy rules for the strict separation of healthcare data of different privacy levels with the desire of many recipients of healthcare information for analysis and other combinations of healthcare data of different privacy levels. As a result of these competing desires, healthcare information systems may adopt a relatively inflexible approach to privacy and consent and may store and utilize healthcare data in a manner that limits data use, even to an extent beyond that required by the privacy levels.

BRIEF SUMMARY

A healthcare information system, method and computer program product are provided in accordance with an example embodiment in order to efficiently receive, process and output healthcare data in a manner that takes into account the data use restrictions associated with the healthcare data, even in instances in which data projections are assembled from a plurality of data elements. The healthcare information system, method and computer program product of an example embodiment also efficiently accounts for time in association with the data elements, such as the time from which each data element of the data projection is valid and the time at which each data element of the data projection becomes invalid, thereby permitting the sequence in which the data elements are received to be of less, if any, importance. The healthcare information system, method and computer program product of an example embodiment also efficiently distributes the healthcare data or data projections based thereupon, by publication to one or more subscribers.

In an example embodiment, a healthcare information system is provided that is configured to control access to a data projection. The healthcare information system includes processing circuitry configured to assemble the data projection from a plurality of data elements. At least some of the data elements have different data use restrictions associated therewith. The processing circuitry is also configured to determine a combined data use restriction for the data projection based upon the data use restrictions of the data elements from which the data projection is assembled. The processing circuitry is further configured to associate metadata with the data projection. The metadata includes the combined data use restriction. Further, the processing circuitry of this example embodiment is configured to control access to the data projection in accordance with the combined data use restriction maintained by the metadata associated with the data projection.

The processing circuitry of an example embodiment is configured to determine the combined data use restriction by determining a combined caching restriction based upon respective caching restrictions of the data elements from which the data projection is assembled. In this example embodiment, the processing circuitry may be further configured to cause the data projection to be rendered invalid in response to expiration of the combined caching restriction.

The healthcare information system of an example embodiment also includes a file store configured to store the data elements. In this example embodiment, the processing circuitry is also configured to associate metadata with respective data elements with the metadata including time data associated with the respective data element. In an example embodiment, the file store is configured to store the data elements by storing a respective data element a single time even though the respective data element is received a plurality of times. In this example embodiment, the processing circuitry is configured to associate metadata with the respective data element by providing an indication within the metadata of the plurality of times that the respective data element was received. In an example embodiment, the time data includes a time from which the respective data element is valid, a time at which the respective data element becomes invalid, and a time from which the respective data element was known. In this example embodiment, the processing circuitry is configured to determine the combined data use restriction based upon the time from which each data element of the data projection is valid and the time at which each data element of the data projection becomes invalid.

The processing circuitry of the healthcare information system of an example embodiment is further configured to create an event based upon one or a combination of data elements. In this example embodiment, the processing circuitry is further configured to determine whether a subscriber is able to be notified of the event based upon the combined data use restriction. In an instance in which the subscriber is determined to be able to be notified by the event, the processing circuitry is further configured to publish the event. In an example embodiment, the processing circuitry is configured to create an event by determining that the event is to be created based upon a comparison of metadata associated with the one or the combination of data elements to a definition of the event.

In another example embodiment, a method of controlling access to a data projection is provided that includes assembling the data projection from a plurality of data elements. At least some of the data elements have different data use restrictions associated therewith. The method of this example embodiment also includes determining a combined data use restriction for the data projection based upon the data use restrictions of the data elements from which the data projection is assembled. The method of this example embodiment also includes associating metadata with the data projection. The metadata includes the combined data use restriction. In this example embodiment, the method further includes controlling access to the data projection in accordance with the combined data use restriction maintained by the metadata associated with the data projection.

The method of an example embodiment determines the combined data use restriction by determining a combined caching restriction based upon the respective caching restrictions of the data elements from which the data projection is assembled. In this example embodiment, the method also includes causing the data projection to be rendered invalid in response to expiration of the combined caching restriction.

The method of an example embodiment also includes storing the data elements and associating metadata with respective data elements with the metadata including time data associated with the respective data element. In an example embodiment, the method stores the data elements by storing a respective data element a single time even though the respective data element is received a plurality of times. In this example embodiment, the method associates metadata with the respective data element by providing an indication within the metadata of the plurality of times that the respective data element was received. In an example embodiment, the time data includes a time from which the respective data element is valid, a time at which the respective data element becomes invalid, and a time from which the respective data element was known. In this example embodiment, the method determines the combined data use restriction based upon the time from which each data element of the data projection is valid and the time at which each data element of the data projection becomes invalid.

The method of an example embodiment also includes creating an event based upon a respective data element and determining whether a subscriber is able to be notified of the event based upon the combined data use restriction. In an instance in which the subscriber is determined to be able to be notified of the event, the method of this example embodiment publishes the event. In accordance with an example embodiment, the creation of the event includes determining that the event is to be created based upon a comparison of metadata associated with the respective data element to a definition of the event.

In a further example embodiment, a computer program product is provided for controlling access to a data projection. The computer program product includes at least one non-transitory computer-readable storage medium having computer-executable program code portions stored therein with the computer-executable program code portions including program code instructions for assembling the data projection from a plurality of data elements. At least some of the data elements have different data use restrictions associated therewith. The computer-executable program code portions also include program code instructions for determining a combined data use restriction for the data projection based upon the data use restrictions of the data elements from which the data projection is assembled. The computer-executable program code portions also include program code instructions for associating metadata with the data projection. The metadata includes the combined data use restriction. In this example embodiment, the computer-executable program code portions also include program code instruction for controlling access to the data projection in accordance with the combined data use restriction maintained by the metadata associated with the data projection.

In an example embodiment, the program code instruction for determining the combined data use restrictions include program code instruction for determining a combined caching restriction based upon respective caching restrictions of the data elements from which the data projection is assembled. In another example embodiment, the computer-executable program code portions further include program code instructions for storing the data elements and associating metadata with respective data elements with the metadata including time data associated with the respective data element. In this example embodiment, the program code instructions for storing the data elements include program code instructions for storing a respective data element a single time even though the respective data element is received a plurality of times. Additionally, the program code instructions for associating metadata with the respective data element include program code instructions for providing an indication within the metadata of the plurality of times that the respective data element was received.

In an example embodiment, the computer-executable program code portions further include program code instructions for creating an event based upon a respective data element and determining whether a subscriber is able to be notified of the event based upon the combined data use restriction. In an instance in which the subscriber is determined to be able to be notified of the event, the computer-executable program code portions of this example embodiment may also include program code instructions for publishing the event.

BRIEF DESCRIPTION OF THE DRAWINGS

Having thus described aspects of the present disclosure in general terms, reference will now be made to the accompanying drawings, which are not necessarily drawn to scale, and wherein:

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information" and similar terms may be used interchangeably to refer to data capable of being transmitted, received and/or stored in accordance with embodiments of the present invention. Thus, use of any such terms should not be taken to limit the spirit and scope of embodiments of the present invention.

A healthcare information system, method and computer program product are provided in accordance with an example embodiment in order to efficiently receive, process and distribute healthcare data in a manner that respects the privacy level and corresponding confidentiality requirements associated with the various types of healthcare data. In an example embodiment, the healthcare information system, method and computer program product are configured to control access to a data projection in a manner that is consistent with the privacy levels of the data included within the data projection. As such, the healthcare information system, method and computer program product of this example embodiment can perform a variety of analytics upon the healthcare data while continuing to ensure compliance with the privacy levels of the constituent data elements.

In an example embodiment, the healthcare information system, method and computer program product are also configured to create and publish an event based upon one or a combination of data elements. However, the healthcare information system, method and computer program product of this example embodiment are configured to ensure that the one or more data elements upon which the event is based are able to be published and also that the subscriber is entitled to receive the event based upon the one or more data elements prior to publishing the event, thereby balancing privacy concerns in the data elements with the interest of subscribers to receive notice of various events relating to the data elements. Further, the healthcare information system, method and computer program product of an example embodiment may associate metadata with the respective data elements with the metadata including time data associated with the respective data element. As such, the healthcare information system, method and computer program product of this example embodiment may ensure that a data element is relevant for a particular period of time and/or understand the chronological relationship of the data element to other data elements.

Figure 1:
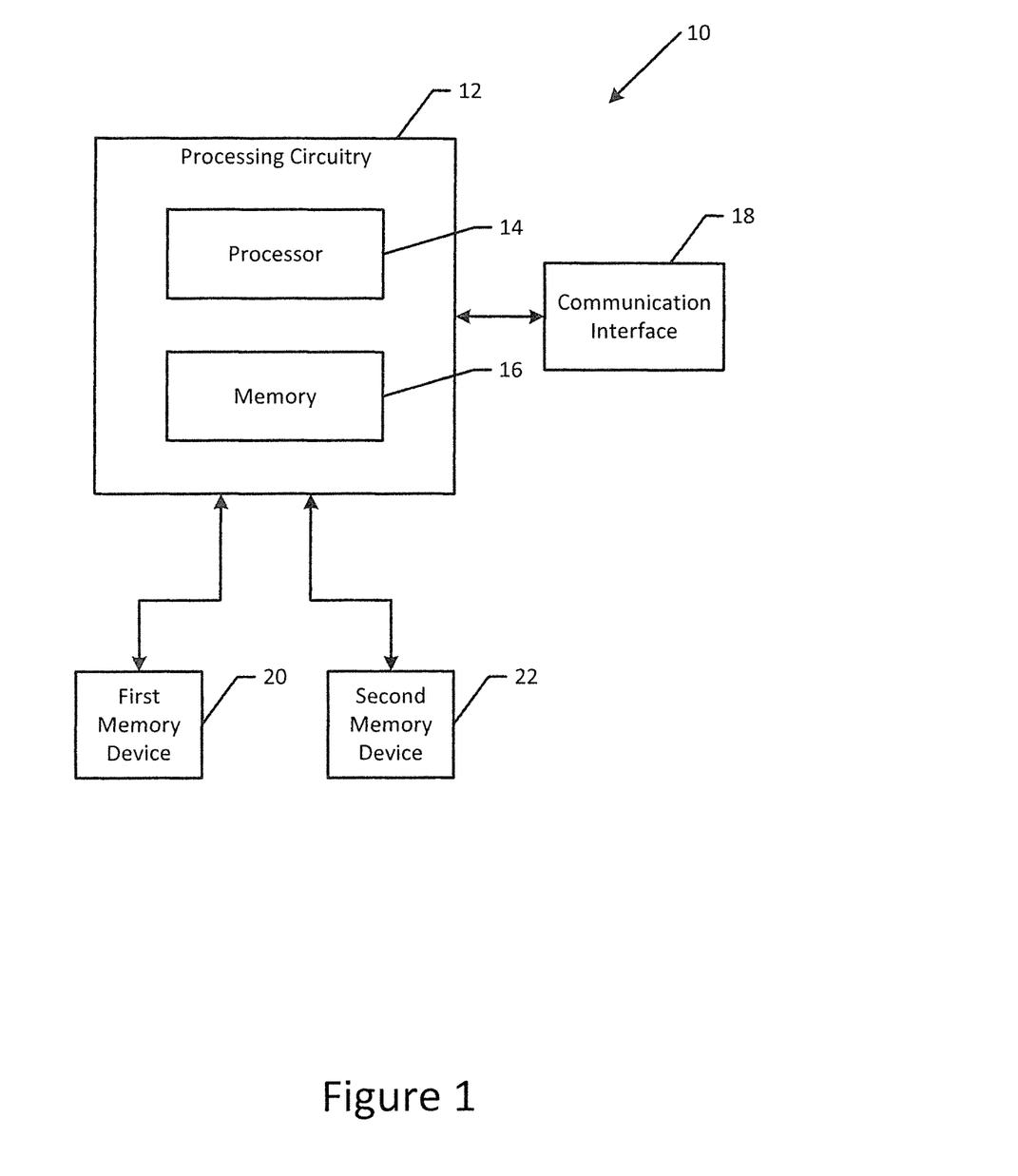
FIG. 1 is a block diagram of a healthcare information system that may be specifically configured in accordance with an example embodiment of the present invention.

The healthcare information system may be configured in various manners. As shown in FIG. 1, the healthcare information system 10 of an example embodiment may be embodied by a variety of different computer systems that are configured to receive, process and output healthcare information. Regardless of the type of computer system that embodies the healthcare information system, the healthcare information system includes or is associated and in communication with processing circuitry 12 that is configurable to perform functions in accordance with one or more example embodiments disclosed herein. In this regard, the processing circuitry may be configured to perform and/or control performance of one or more functionalities of the healthcare information system in accordance with various example embodiments, and thus may provide means for performing functionalities of the computing device. The processing circuitry may be configured to perform data processing, application execution and/or other processing and management services according to one or more example embodiments.

In some example embodiments, the processing circuitry 12 includes a processor 14 and, in some embodiments, such as that illustrated in FIG. 1, further includes memory 16. The processing circuitry may also be in communication with or otherwise control a communication interface 18 for communicating with other computing systems. As such, the processing circuitry may be embodied as a circuit chip (e.g., an integrated circuit chip) configured (e.g., with hardware, software or a combination of hardware and software) to perform operations described herein.

The processor 14 may be embodied in a number of different ways. For example, the processor may be embodied as various processing means such as one or more of a central processing unit, a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device as described herein. The plurality of processors may be embodied on a single computing device or distributed across a plurality of computing devices collectively configured to function as the computing device. In some example embodiments, the processor may be configured to execute instructions stored in the memory 16 or otherwise accessible to the processor. As such, whether configured by hardware or by a combination of hardware and software, the processor may represent an entity (e.g., physically embodied in circuitry—in the form of processing circuitry 12) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

The processing circuitry 12 may also include memory 16 as shown in FIG. 1. In some example embodiments, the memory may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The memory may be configured to store information, data, applications, instructions and/or the like for enabling the computing device to carry out various functions in accordance with one or more example embodiments. For example, the memory may be configured to buffer input data for processing by the processor 14. Additionally or alternatively, the memory may be configured to store instructions for execution by the processor. Among the contents of the memory, applications may be stored for execution by the processor in order to carry out the functionality associated with each respective application. In some cases, the memory may be in communication with the processor via a bus or buses for passing information among components of the healthcare information system 10.

As noted above, the healthcare information system 10 of the embodiment of FIG. 1 also includes a communication interface 18. The communication interface is configured to communicate with one or more subscribers in order to affect the delivery of messages thereto. Additionally, the communication interface of an example embodiment may be in communication with one or more sources of messages so as to receive the messages therefrom, which are then to be delivered to the respective subscribers. The communication interface may be any means such as a device or circuitry embodied in either hardware or a combination of hardware and software that is configured to receive and/or transmit messages from sources to subscribers. In this regard, the communication interface may include, for example, an antenna (or multiple antennas) and supporting hardware and/or software for enabling communications with a wireless communication network. Additionally or alternatively, the communication interface may include the circuitry for interacting with the antenna(s) to cause transmission of signals via the antenna(s) or to handle receipt of signals received via the antenna(s). In some environments, the communication interface may alternatively or also support wired communication.

The communication interface 18 may be configured to directly and/or indirectly communicate with the sources of messages and/or the subscribes in any of a number of different manners including, for example, any of a number of wireline or wireless communication or networking techniques. Examples of such techniques include, without limitation, Universal Serial Bus (USB), radio frequency (RF), Bluetooth (BT), infrared (IrDA), any of a number of different cellular (wireless) communication techniques such as any of a number of 2G, 2.5G, 3G, 4G or Long Term Evolution (LTE) communication techniques, local area network (LAN), wireless LAN (WLAN) techniques or the like. In accordance with various ones of these techniques, the communication interface can be coupled to and configured to communicate across one or more networks. The network (s) can comprise any of a number of different combinations of one or more different types of networks, including data and/or voice networks. For example, the network(s) can include one or more data networks, such as a LAN, a metropolitan area network (MAN), and/or a wide area network (WAN) (e.g., Internet), and include one or more voice networks, such as a public-switched telephone network (PSTN).

As shown in FIG. 1, the healthcare information system 10 may also include a plurality of additional memory devices in communication with the processing circuitry 12. For example, the healthcare information system may include first and second memory devices 20, 22 as depicted in FIG. 1, although the healthcare information system may include additional memory devices in other example embodiments. The plurality of memory devices, such as the first and second memory devices, may include different types of memory devices depending upon the type of information to be stored by the memory device and the access requirements for the type of information. As described below in conjunction with the embodiment of FIG. 2, for example, the first memory device may serve as a file store and, as such, may be embodied by a type of memory configured to store large amounts of information in an efficient manner, such as a binary large object (BLOB) storage, and the second memory device may be embodied by a key value store or other type of storage configured to efficiently store and access tabular information.

Figure 2:
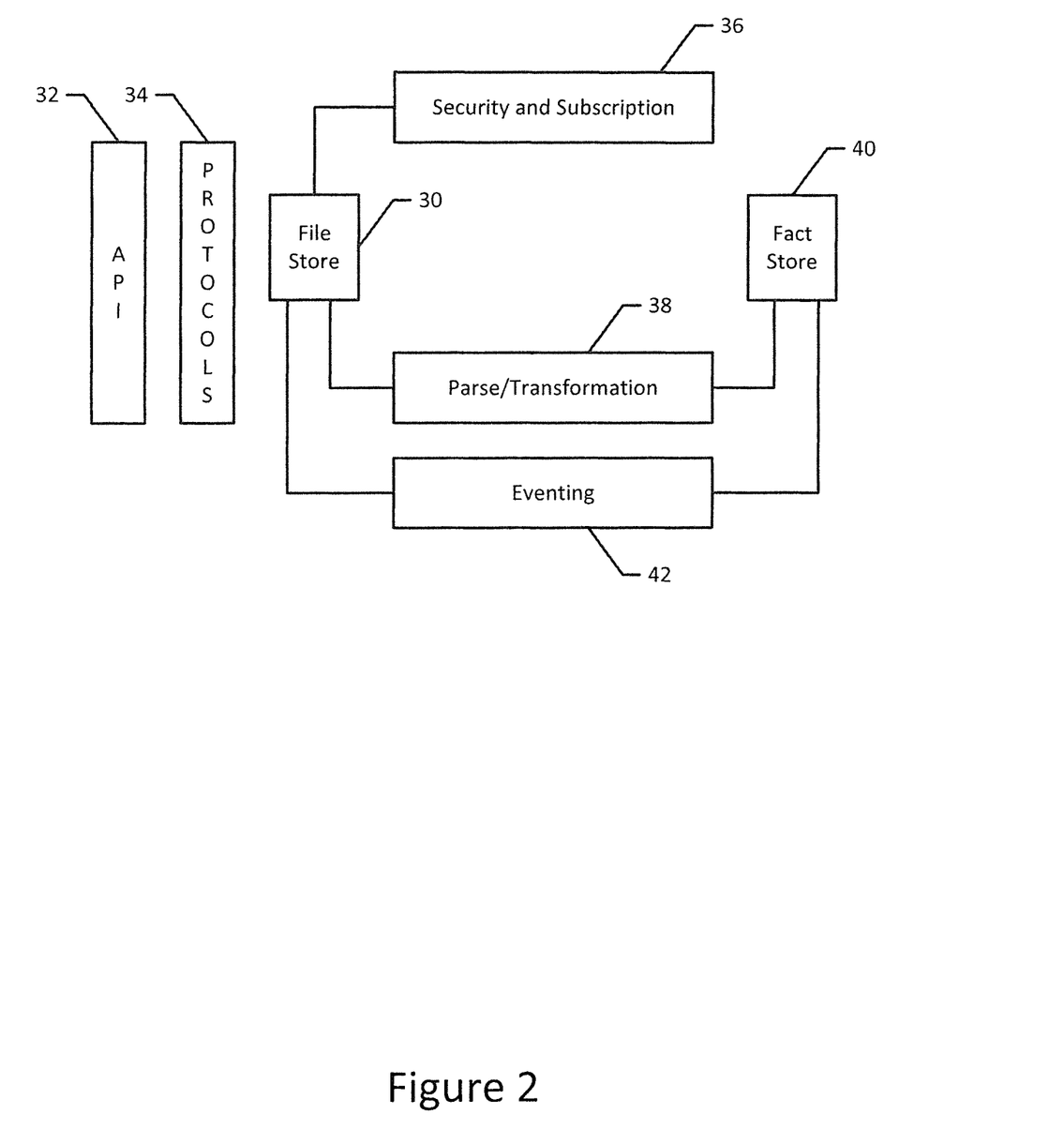
FIG. 2 is a more detailed block diagram of a healthcare information system that may be specifically configured in accordance with an example embodiment of the present invention.

Referring now to FIG. 2, the healthcare information system 10 in accordance with an example embodiment is depicted. The healthcare information system of the embodiment of FIG. 2 receives data via an application programming interface (API) 32 that may be embodied, for example, by the communication interface 18, the processing circuitry 12, such as the processor 14, or the like. Prior to storing the data elements that are received via the API within the file store 30, the healthcare information system may subject the data to one or more protocols 34 in order to obtain a normalized set of facts. The protocols may also be defined and/or implemented by the communication interface, the processing circuitry, such as the processor, or the like. In this regard, the protocols may identify the parse and/or transformation logic to be applied to the data in order to obtain a normalized set of facts. The protocols may be based upon the type of data, the data source and/or the eventual recipient of the data. In this regard, some protocols may apply to all data types. For example, the same protocol may apply to the definition of a person, the definition of an address, etc. regardless of the type of data within which the person or address is defined. In contrast, other protocols are specific to a particular data type or a particular source or intended recipient of the data.

The healthcare information system 10 of this example embodiment also includes a file store 30 for storing the data received via the API 32 once the corresponding protocols 34 have identified the parse and transformation logic to be associated with the data element. The file store may be embodied by the first memory device 20 and, in one embodiment, is embodied by a type of memory device that efficiently stores large amounts of information, such as BLOB storage. In an example embodiment, the data is hashed, such as by the processing circuitry 12, e.g., the processor 14, prior to storage by the file store.

The data received by the healthcare information system 10 may be encrypted or otherwise secured, such as with an asymmetric encryption technique utilizing public and private keys. In order to enhance the security associated with the data, the keys may be rotated over the course of time. As such, the healthcare information system may include security and subscription logic 36, such as may be embodied by the processing circuitry 12, such as the processor 14. As described above, the healthcare information system also includes parse and transformation logic 38, such as may also be embodied by the processing circuitry, such as the processor. The manner in which a data element is to be processed by the parse and transformation logic is defined by a protocol based upon the data type and/or the data source and intended recipient. The parse and transformation logic is configured to normalize the data element so as to produce a normalized set of facts. The normalized set of facts may be stored, for example, by the fact store 40. In this regard, the fact store may be embodied by a different memory device than the memory device that embodies the file store 30. In this regard, the fact store may be embodied by the second memory device 22 which may be embodied by a type of memory device that efficiently creates and accesses tables, such as a key value store. In addition to the set of normalized facts generated by the parse and transformation logic, the fact store may store a pointer to the location within the file store at which the underlying data elements are stored.

As described below, the healthcare information system 10 of an example embodiment is also configured to create and publish events based upon one or a combination of the data elements. As such, the healthcare information system of this example embodiment includes eventing logic 42, such as may be embodied by the processing circuitry 12, such as the processor 14.

Figure 3:
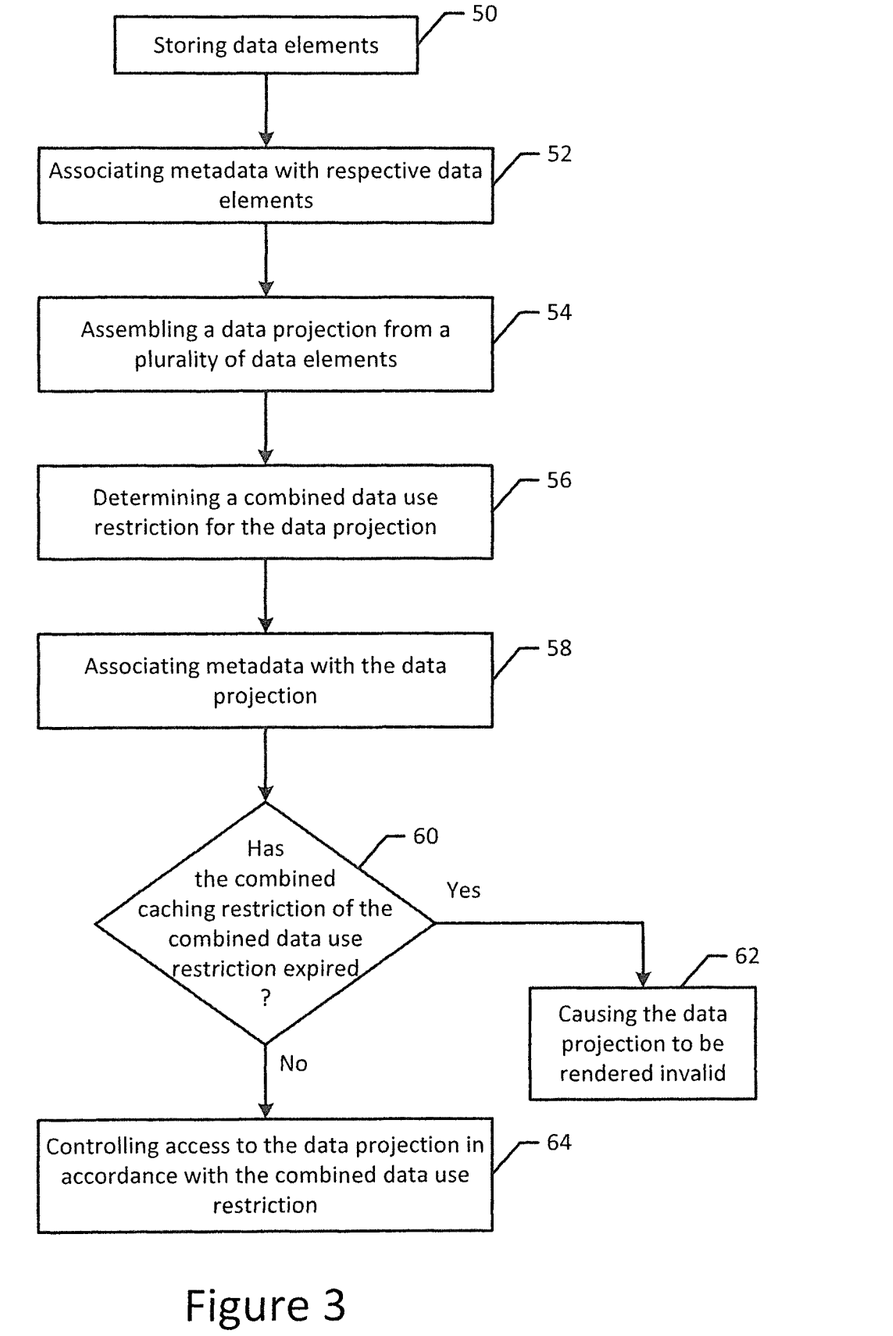
FIG. 3 is a flowchart of the operations performed, such as by the healthcare information system of FIG. 1 or 2, for controlling access to a data projection in accordance with an example embodiment of the present invention.

The operations performed by a healthcare information system 10 and method in accordance with an example embodiment are depicted in FIG. 3. As shown in block 50, the healthcare information system includes means, such as the processing circuitry 12, such as the processor 14, the first memory device 20, the file store 30 or the like, for storing the data elements received from various data sources. As described above, the data elements are received via an API 32 and may be decrypted by the security and subscription logic 36 prior to being stored. In addition, the healthcare information system may include protocols 34 for associating respective parse and transformation logic with the data elements based, for example, upon the data type of the data elements. The parse and transformation logic identified by the protocol associated with the respective data type of the data elements generates a normalized set of facts representative of the data elements, such as for storage by the fact store 40.

In addition to storing the data elements, metadata is associated with the respective data elements and is stored in relation thereto, such as by the first memory device 20, the file store 30, etc. As shown in block 52 of FIG. 3, the healthcare information system 10 includes means, such as the processing circuitry 12, e.g., the processor 14, or the like, for associating metadata with the respective data elements. The metadata may include a plurality of attributes associated with the data element including an indication of the data source, the data type, and time data associated with the respective data element. In this regard, the time data may include business domain dates defining the time from which the data element is valid and the time to which the data element is valid. In addition, the time data may include system domain dates, such as the time from which the respective data element was known by the healthcare information system. In instances in which the data element is only known by the healthcare information system for a limited time, such as in an instance in which the data element is corrected at some time following the initial receipt and storage of the data element, the time data may also include a time to which the respective data element was known.

The time data may be provided by the data source of the respective data element. For example, the healthcare information system 10, such as the processing circuitry 12, such as the processor 14, may be configured to identify the time from which the data element is valid. A time stamp associated with the data element provided by a data source may identify the time from which the data element was valid and the time of receipt of the data element by the healthcare information system may serve as the time from which the data element was known.

In some instances, a respective data element is received a plurality of times, such as from different data sources or repeatedly from the same data source. In this example embodiment, the healthcare information system 10, such as the processing circuitry 12, is configured to store the respective data element a single time, such as within the file store 30. In this example embodiment, the metadata associated with the data element may include an indication of the number of times that a respective data element was received and, in some instances, the data sources from which the respective data element was received and the times of receipt from the respective data sources.

As shown in block 54, the healthcare information system 10 also includes means, such as the processing circuitry 12, e.g., the processor 14, or the like, for assembling a data projection from a plurality of data elements. In this regard, the processing circuitry, such as the processor, is configured to assemble the data projection by combining a plurality of data elements, such as in a predefined manner, in order to create the data projection. Various types of data projections may be defined including data projections based upon the analysis or other processing of the plurality of data elements. For example, the data projection may be a weighted time average of a data value with more recent data values being weighted more greatly than older data values. Alternatively, a data projection may identify the number of instances in which a particular combination of different types of data has respective values that satisfy predefined thresholds.

By way of example but not of limitation, a data projection that is determined in response to the receipt of a glucose reading is an average glucose reading for the patient over the past 90 days. Other examples of data projections that are determined in response to the receipt of a glucose reading and the comparison of the glucose reading (or the 90 day average glucose reading) to a predefined threshold relating to being at risk for diabetes may include analytics that define the geographic distribution of patients that have been determined to be at risk for diabetes and/or the percentage of a practice's patient population to have been determined to be at risk for diabetes.

Regardless of the type of data projection, at least some of the data elements that are incorporated within the data projection have different data use restrictions associated therewith. The data use restrictions associated with the respective data elements limit the use of the respective data element, such as by limiting the recipients to which the data element may be provided. In addition or alternatively, the data use restrictions may include caching or time-to-live (TTL) restrictions that limit the time period for which the data element is valid and may be relied upon in conjunction with the assembly of a data projection.

As shown in block 56 of FIG. 3, the healthcare information system 10 of an example embodiment also includes means, such as the processing circuitry 12, e.g., the processor 14, or the like, for determining a combined data use restriction for the data projection based upon the data use restrictions of the data elements from which the data projection is assembled. In an example embodiment, the processing circuitry, such as the processor, is configured to analyze the data use restrictions of the data elements from which the data projection is assembled and to identify each of the different types of data use restrictions associated with the data elements. For each different type of data use restriction, the processing circuitry, such as the processor, is also configured to determine the most restrictive, e.g., the most limiting, of the data use restrictions and to combine the most restrictive data use restriction of each type of data use restriction associated with the data elements from which the data projection is assembled to create the combined data use restriction for the data projection. As such, compliance with the combined data use restriction for the data projection will ensure compliance with the different data use restrictions associated with the data elements from which the data projection was assembled. However, compliance with the combined data use restriction for the data projection will not impose any data use restriction that is not imposed upon at least one of the individual data elements from which the data projection was assembled. One example of a combined data use restriction is a combined caching restriction that defines the time period for which the data projection is considered valid and may be relied upon in conjunction with the assembly of a data projection. In this example, the combined caching restriction is based upon the caching or TTL restrictions associated with the individual data elements from which the data projection was assembled with the combined caching restriction associated with the data projection at least as restrictive or limiting as and, in some embodiments, equal to the most restrictive or limiting of the caching or TTL restrictions associated with the individual data elements from which the data projection was assembled.

Following assembly, the data projection may be stored, such as by the second memory device 22, the fact store 30 or the like. In addition, the healthcare information system 10 may include means, such as the processing circuitry 12, such as the processor 14, or the like, for associating metadata with the data projection. See block 58 of FIG. 3. The metadata includes the combined data use restriction and may also be stored, such as by the second memory device, the fact store or the like.

Prior to providing the data projection, the healthcare information system 10, such as the processing circuitry 12, e.g., the processor 14, is configured to determine whether the combined caching restriction or the combined data use restriction has expired. See block 60 of FIG. 3. In an instance in which the combined caching restriction of the combined data use restriction associated with the data projection has expired, the healthcare information system, such as the processing circuitry, e.g., the processor, is configured to cause the data projection to be rendered invalid such that the data projection is not provided to a recipient as valid data. See block 62. In this instance, the healthcare information system of an example embodiment, such as the processing circuitry, e.g., the processor, is configured to cause the data projection to be re-computed utilizing data elements that are currently effective with the newly computed data projection being provided if the combined data use restriction for the newly computed data projection is satisfied.

However, in an instance in which the combined caching restriction of the combined data use restriction associated with the data projection is not expired, the healthcare information system 10 includes means, such as the processing circuitry 12, e.g., the processor 14, or the like, for controlling access to the data projection in accordance with the combined data use restriction maintained by the metadata associated with the data projection. See block 64. In this regard, the processing circuitry is configured to permit access to the data projection or to otherwise provide the data projection to one or more recipients so long as the provision of the data projection complies with the combined data use restriction associated therewith. In addition to including a combined caching restriction that defines the time at which the data projection expires, the combined data use restriction may restrict the recipients to which the data projection may be provided and/or the purposes for which the data projection may be utilized.

Figure 4:
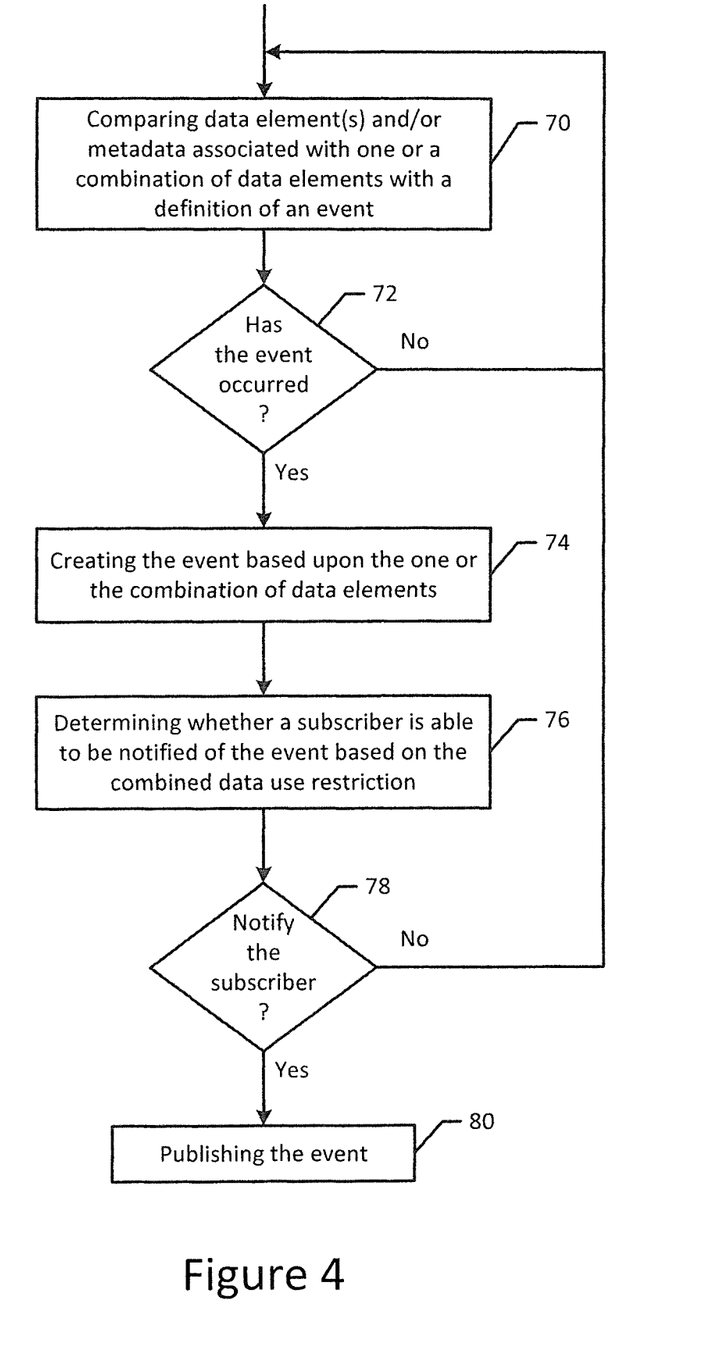
FIG. 4 is a flowchart illustrating operations performed, such as by the healthcare information system of FIG. 1 or 2, for selectively creating and publishing an event in accordance with an example embodiment of the present invention.

As noted above, the healthcare information system 10 of an example embodiment is configured to create and publish events based upon one or a combination of data elements, and/or metadata associated therewith. Events may be defined in various manners. For example, an event may be defined such that a subscriber is notified when a particular type of data or projection is available for a specific patient or a population of patients of interest, e.g., an event may be defined in an instance in which an update to a summarized data set for clinical quality measures (CQMs) is available. As another example, an event may be defined in an instance in which the metadata indicates a data element is associated with a particular geolocation, thereby permitting summary statistics to be calculated by location. Further, an event may be defined based upon a composite calculation, e.g., an event may be defined to identify a data element associated with a previously controlled diabetic with a HbA1C value of greater than 9% who was recently seen at a healthcare location.

With respect to the creation and publication of events, FIG. 4 depicts the operations performed in conjunction with the creation and publication of events in accordance with an example embodiment. As shown in blocks 70 and 72, the healthcare information system 10 of an example embodiment includes the means, such the processing circuitry 12, e.g., the processor 14, the eventing logic 42, or the like, for comparing one or a combination of data elements, e.g., a data projection, with a definition of an event and based upon that comparison determining if the event has occurred. In addition to or instead of comparing the data elements or a combination thereof, metadata associated with one or a combination of data elements may be compared with the definition of an event to determine if the event has occurred. In this regard, events may be defined by various combinations of attributes associated with one or a combination of data elements. For example, an event may be defined by a plurality of different types of data elements, each of which has at least a respective predefined value. In an instance in which the event is determined to have not occurred, the healthcare information system, such as the processing circuitry, is configured to continue to monitor the data that is received and the data projections that are assembled therefrom and/or the metadata associated therewith to determine if an event subsequently occurs.

However, in an instance in which an event is determined to have occurred, the healthcare information system 10 of this example embodiment includes means, such as the processing circuitry 12, the processor 14, the eventing logic 42 or the like, for creating the event based upon the one or the combination of data elements. See block 74 of FIG. 4. For example, in an instance in which an event is defined following the receipt of ten data elements from a respective data source, the corresponding event may be created by determining the time average of the data elements received from the data source. The healthcare information system of this example embodiment also includes means, such as the processing circuitry, the processor, the eventing logic or the like, for determining whether a subscriber is able to be notified of the event based upon the combined data use restriction. See blocks 76 and 78. In this regard, the processing circuitry is configured to determine if the subscriber is able to be notified of the event while still satisfying the combined data use restriction associated with the underlying data elements. In an instance in which it is determined that the combined data use restriction prevents a subscriber from being notified, the healthcare information system, such as the processing circuitry, continues to monitor the data element for the occurrence of an event. However, in an instance in which the subscriber is determined to be able to be notified of the event, the healthcare information system of this example embodiment includes means, such as the processing circuitry, the processor, the communication interface 18, the eventing logic or the like, for publishing the event to the respective subscriber. See block 80. As such, a subscriber may efficiently and timely receive notification of an event that has been identified by the subscriber to be of interest.

The healthcare information system 10, method and computer program product of an example embodiment therefore provide for the receipt, processing and provision of healthcare data and data projections based upon the healthcare data in a manner that permits efficient access to the healthcare data by one or more subscribers and that does so in a manner that is consistent with the privacy levels associated with the various data elements. In addition to notifying subscribers of predefined events, a subscriber may also query the healthcare information system for particular data elements or for particular combinations of data elements, such as based upon an analysis of the underlying healthcare data, in order to obtain healthcare information of import to the subscriber.

As described above, FIGS. 3 and 4 are flowcharts of a healthcare information system 10, method and computer program product according to example embodiments of the invention. It will be understood that each block of the flowcharts, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 16 and executed by processor 14 of the healthcare information system. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowcharts support combinations of means for performing the specified functions and combinations of steps for performing the specified functions. It will also be understood that one or more blocks of the flowcharts, and combinations of blocks in the flowcharts, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 12 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A health care information system configured to control access to a data projection, the health care information system comprising:
a first memory device comprising a file store configured to store a plurality of data elements, wherein at least some of the data elements comprise readings of one or more patient parameters;
processing circuitry configured to:
decrypt the plurality of data elements using one of a plurality of paired public and private keys, the plurality of paired public and private keys being rotated over time;
assemble the data projection from the plurality of data elements by combining a plurality of data elements to create the data projection, wherein the data projection is based upon an analysis or other processing of the plurality of data elements, and wherein at least some of the data elements have different data use restrictions associated therewith;
analyze the data use restrictions of the data elements from which the data projection is assembled to identify two or more types of data use restrictions;
determine, for the two or more types of data use restrictions that are identified, the most restrictive data use restriction;
determine a combined data use restriction for the data projection based upon the data use restrictions of the data elements from which the data projection is assembled, wherein the combined data use restriction is the most restrictive data use restriction, and wherein the combined data use restriction is different than the data use restriction of one or more data elements from which the data projection is assembled;
associate metadata with the data projection, wherein the metadata includes the combined data use restriction, the metadata being unrestricted with respect to use; and
control access to the data projection in accordance with the combined data use restriction maintained by the metadata associated with the data projection; and
a second memory device configured to store the data projection assembled by the processing circuitry, wherein the second memory device is of a different type than the first memory device.

2. A health care information system according to claim 1 wherein the processing circuitry is configured to determine the combined data use restriction by determining a combined caching restriction based upon respective caching restrictions of the data elements from which the data projection is assembled.

3. A health care information system according to claim 2 wherein the processing circuitry is further configured to cause the data projection to be rendered invalid in response to expiration of the combined caching restriction.

4. A health care information system according to claim 1 wherein the processing circuitry is configured to associate metadata with respective data elements, wherein the metadata includes time data associated with the respective data element.

5. A health care information system according to claim 4 wherein the file store is configured to store the data elements by storing a respective data element a single time even though the respective data element is received a plurality of times, and wherein the processing circuitry is configured to associate metadata with the respective data element by providing an indication within the metadata of the plurality of times that the respective data element was received.

6. A health care information system according to claim 4 wherein the time data comprises a time from which the respective data element is valid, a time at which the respective data element becomes invalid and a time from which the respective data element was known, and wherein the processing circuitry is configured to determine the combined data use restriction by determining the combined data use restriction based upon the time from which each data element of the data projection is valid and the time at which each data element of the data projection becomes invalid.

7. A health care information system according to claim 1 wherein the processing circuitry is further configured to:
create an event based upon one or a combination of data elements;
determine whether a subscriber is able to be notified of the event based upon the combined data use restriction; and
in an instance in which the subscriber is determined to be able to be notified of the event, publish the event.

8. A health care information system according to claim 7 wherein the processing circuitry is configured to create an event by determining that the event is to be created based upon a comparison of metadata associated with the one or the combination of data elements to a definition of the event.

9. A method implemented by a health care information system for controlling access to a data projection, the method comprising:
storing a plurality of data elements in a first memory device of the health care information system, wherein the first memory device comprises a file store, and wherein at least some of the data elements comprise readings of one or more patient parameters;
decrypting the plurality of data elements using one of a plurality of paired public and private keys, the plurality of paired public and private keys being rotated over time;
assembling the data projection from the plurality of data elements by combining a plurality of data elements to create the data projection, wherein the data projection is based upon an analysis or other processing of the plurality of data elements, and wherein at least some of the data elements have different data use restrictions associated therewith;
storing the data projection in a second memory device of the health care information system, wherein the second memory device comprises a key value store, further comprising at least a plurality of sets of paired public and private keys, and is of a different type than the first memory device;
analyzing the data use restrictions of the data elements from which the data projection is assembled to identify two or more types of data use restrictions;
determining, for the two or more types of data use restrictions that are identified, the most restrictive data use restriction;
determining a combined data use restriction for the data projection based upon the data use restrictions of the data elements from which the data projection is assembled, wherein the combined data use restriction is the most restrictive data use restriction, and wherein the combined data use restriction is different than the data use restriction of one or more data elements from which the data projection is assembled;
associating metadata with the data projection, wherein the metadata includes the combined data use restriction, the metadata being unrestricted with respect to use; and
controlling access to the data projection in accordance with the combined data use restriction maintained by the metadata associated with the data projection.

10. A method according to claim 9 wherein determining the combined data use restriction comprises determining a combined caching restriction based upon respective caching restrictions of the data elements from which the data projection is assembled.

11. A method according to claim 10 further comprising causing the data projection to be rendered invalid in response to expiration of the combined caching restriction.

12. A method according to claim 9 further comprising:
associating metadata with respective data elements, wherein the metadata includes time data associated with the respective data element.

13. A method according to claim 12 wherein storing the data elements comprises storing a respective data element a single time even though the respective data element is received a plurality of times, and wherein associating metadata with the respective data element comprises providing an indication within the metadata of the plurality of times that the respective data element was received.

14. A method according to claim 12 wherein the time data comprises a time from which the respective data element is valid, a time at which the respective data element becomes invalid and a time from which the respective data element was known, and wherein determining the combined data use restriction comprises determining the combined data use restriction based upon the time from which each data element of the data projection is valid and the time at which each data element of the data projection becomes invalid.

15. A method according to claim 9 further comprising:
creating an event based upon one or a combination of data elements;
determining whether a subscriber is able to be notified of the event based upon the combined data use restriction; and
in an instance in which the subscriber is determined to be able to be notified of the event, publishing the event.

16. A method according to claim 15 wherein creating an event comprises determining that the event is to be created based upon a comparison of metadata associated with the one or the combination of data elements to a definition of the event.

17. A computer program product of a health care information system for controlling access to a data projection, the computer program product comprising at least one non-transitory computer-readable storage medium having computer-executable program code portions stored therein, the computer-executable program code portions comprising program code instructions for:
storing a plurality of data elements in a first memory device of the health care information system, wherein the first memory device comprises a file store, and wherein at least some of the data elements comprise readings of one or more patient parameters;
decrypting the plurality of data elements using one of a plurality of paired public and private keys, the plurality of paired public and private keys being rotated over time;
assembling the data projection from the plurality of data elements by combining a plurality of data elements to create the data projection, wherein the data projection is based upon an analysis or other processing of the plurality of data elements, and wherein at least some of the data elements have different data use restrictions associated therewith;
storing the data projection in a second memory device of the health care information system, wherein the second memory device comprises a key value store, further comprising at least a plurality of sets of paired public and private keys, and is of a different type than the first memory device;
analyzing the data use restrictions of the data elements from which the data projection is assembled to identify two or more types of data use restrictions;
determining, for the two or more types of data use restrictions that are identified, the most restrictive data use restriction;
determining a combined data use restriction for the data projection based upon the data use restrictions of the data elements from which the data projection is assembled, wherein the combined data use restriction is the most restrictive data use restriction, and wherein the combined data use restriction is different than the data use restriction of one or more data elements from which the data projection is assembled;
associating metadata with the data projection, wherein the metadata includes the combined data use restriction, the metadata being unrestricted with respect to use; and
controlling access to the data projection in accordance with the combined data use restriction maintained by the metadata associated with the data projection.

18. A computer program product according to claim 17 wherein the program code instructions for determining the combined data use restriction comprise program code instructions for determining a combined caching restriction based upon respective caching restrictions of the data elements from which the data projection is assembled.

19. A computer program product according to claim 17 wherein the computer-executable program code portions further comprise program code instructions for:
associating metadata with respective data elements, wherein the metadata includes time data associated with the respective data element,
wherein the program code instructions for storing the data elements comprise program code instructions for storing a respective data element a single time even though the respective data element is received a plurality of times, and wherein the program code instructions for associating metadata with the respective data element comprise program code instructions for providing an indication within the metadata of the plurality of times that the respective data element was received.

20. A computer program product according to claim 17 wherein the computer-executable program code portions further comprise program code instructions for:
- creating an event based upon one or a combination of data elements;
- determining whether a subscriber is able to be notified of the event based upon the combined data use restriction; and
- in an instance in which the subscriber is determined to be able to be notified of the event, publishing the event.

21. A health care information system according to claim 1 wherein the first memory device comprises a binary large object (BLOB) storage and the second memory device is configured to store and access tabular information.

22. A health care information system according to claim 6, wherein the respective data element is known for a limited time, determined by the difference between the time from which the respective data element is valid and the time at which the respective data element becomes invalid, and the reading of one or more patient parameters of the respective data element is corrected, at some time following an initial receipt time and storage of the respective data element.

23. A method according to claim 14, wherein the respective data element is known for a limited time, determined by the difference between the time from which the respective data element is valid and the time at which the respective data element becomes invalid, and the reading of one or more patient parameters of the respective data element is corrected, at some time following an initial receipt time and storage of the respective data element.

\* \* \* \* \*